United States Patent [19]

Malette et al.

[11] Patent Number: 4,532,134

[45] Date of Patent: * Jul. 30, 1985

[54] METHOD OF ACHIEVING HEMOSTASIS, INHIBITING FIBROPLASIA, AND PROMOTING TISSUE REGENERATION IN A TISSUE WOUND

[76] Inventors: William G. Malette, 667 Parkwood La., Omaha, Nebr. 68132; Herbert J. Quigley, 9511 Mockingbird Dr., Omaha, Nebr. 68127

[*] Notice: The portion of the term of this patent subsequent to Jul. 19, 2000 has been disclaimed.

[21] Appl. No.: 440,039

[22] Filed: Nov. 8, 1982

Related U.S. Application Data

[63] Continuation-in-part of Ser. No. 251,321, Apr. 6, 1981, Pat. No. 4,394,373.

[51] Int. Cl.$^3$ .................. A61K 31/70; A61B 17/04
[52] U.S. Cl. .................. 514/55; 128/334 R; 424/95
[58] Field of Search .................. 424/95, 180; 3/1.4; 128/334 R

[56] References Cited

U.S. PATENT DOCUMENTS 3,632,754  1/1972  Balassa .................. 424/95
3,911,116  10/1975  Balassa .................. 424/95

OTHER PUBLICATIONS

Balassa et al., Chem. Abst., vol. 91, (1979), p. 13962u.
Prudden et al., Chem. Abst., vol. 73, (1970), p. 43828a.
Prudden et al., The Amer. J. of Surgery, vol. 119, May 1970, pp. 560–564.

*Primary Examiner*—Sam Rosen
*Attorney, Agent, or Firm*—Zarley, McKee, Thomte, Voorhees & Sease

[57] ABSTRACT

The method of achieving hemostasis, inhibiting fibroplasia, and promoting tissue regeneration is described wherein a chitosan solution, or water-soluble chitosan in various solid forms is placed in contact with the tissue wound. The chitosan forms a coagulum which prevents bleeding and negates the formation of a blood clot thereby preventing the formation of fibrin strands. The prevention of the formation of fibrin strands prevents the proliferation of fibroblasts and the synthesis of collagen thereby allowing the promotion of normal tissue regeneration. The process described hereinabove results in wound healing with minimal scar formation. The use of chitosan in grafts is contemplated as well as the use of polyglucosamine in wound healing.

16 Claims, 1 Drawing Figure

METHOD OF ACHIEVING HEMOSTASIS, INHIBITING FIBROPLASIA, AND PROMOTING TISSUE REGENERATION IN A TISSUE WOUND

BACKGROUND OF THE INVENTION

This is a continuation-in-part of our co-pending application, Ser. No. 251,321 filed April 6, 1981 now U.S. Pat. No. 4,394,373.

In applicants' earlier application, a method was described for achieving hemostasis. Since the filing of the co-pending application, the inventors have discovered that chitosan may be used to inhibit fibroplasia, and to promote tissue regeneration.

Science has long sought a method to inhibit the synthesis of collagen in wound healing. Much of the work directed to the inhibition of the synthesis of collagen has involved alteration of the biology of collagen by various chemical antagonists. Lower animals do not heal by scar tissue but generate normal structures from pre-existing cells. Usual wound healing begins with a blood clot containing a fibrin network, along which fibroblasts begin the process of fibroplasia. If blood loss is controlled in the presence of a fibrin clot, fibroblasts will be stimulated. Conversely, if blood loss can be controlled in the absence of a fibrin clot, fibroblasts may be not stimulated, and differentiated cells may have the opportunity to replace the lost tissue. It is has therefore been found that a material is needed to control blood loss absent the usual blood clotting factors, and to allow the ingrowth of normal tissue elements.

Prior art teaches that Chitin and some chitin derivatives accelerate tensile strength of wounds by speeding the fibroblastic synthesis of collagen in the first few days of wound healing. For example, see U.S. Pat. Nos. 3,902,268; 3,911,116 and 3,914,413. This topic is also discussed in the May 1970 issue of American Journal of Surgery, pages 560–564. The subject is further discussed in the June 1969 issue of S.G. & O., pages 1321–1326. It should be noted that the prior art only discusses Chitin and certain derivatives thereof which are entirely different than the de-acetylated chitosan employed in the method of this invention and which will be discussed in more detail hereinafter. The basic structure of natural Chitin is a polymer of N-acetyl-glucosamine. Although, Balassa describes several molecular modifications and shortenings of chain lengths, Balassa retains the N-acetyl structure on each monomer.

Therefore, it is a principal object of this invention to describe a method of treating a tissue wound so as to achieve hemostasis, to inhibit fibroplasia, and to promote tissue regeneration.

Still another object of the invention is to provide a method of treating a wound whereby chitosan solution, or solid chitosan sheets, powders, or fibers are placed in contact with a tissue wound thereby forming a coagulum to prevent bleeding and to negate the formation of a blood clot to prevent the formation of fibrin strands which in turn prevents the proliferation of fibroblasts and the synthesis of collagen, thus allowing the promotion of normal tissue regeneration.

Still another object of the invention is to provide a method of inhibiting fibroplasia and promoting tissue regeneration in vascular grafts by placing chitosan in contact with the graft or by incorporating the chitosan in the graft material.

Still another object of the invention is to provide a method of achieving hemostasis.

These and other objects will be apparent to those skilled in the art.

DESCRIPTION OF THE PREFERRED METHOD

Figure 1:
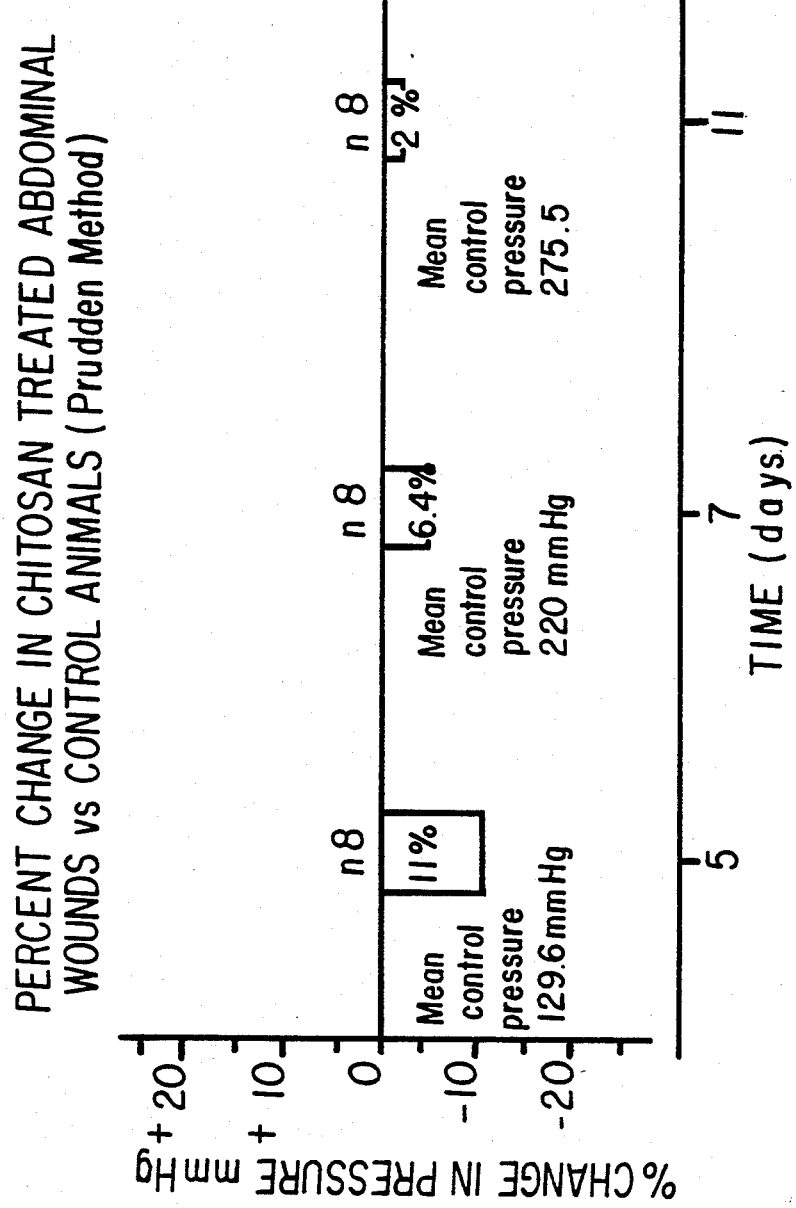
FIG. 1 is a chart which illustrates the results of the chitosan hemostatic solution wound healing evaluation.

As described in Balassa Pat. No. 3,804,949, the term "chitin" embraces naturally occuring chitin, synthetic chitin as well as poly(N-acetylgluosamine) and its epimerpoly(N-acetylgalactosamine). Suitable sources of chitin are from lobsters, shrimp, other crustacea and fungi. Chitosan is a derivative of chitin and the method of preparing chitosan is described in U.S. Pat. No. 3,533,940 and made a part hereof. Chitosan as used herein refers to a de-acetylated chitosan. Analysis of the chitosan material used herein reveals that most of the acetyls (78–92%) have been removed therefrom leaving a very reactive free amine group ($NH_2$) on the second carbon of most of the glucosamine monomers.

The chitosan used in this method is a partially deacetylated chitin and is a partially depolymerized chitin to form a polyglucosamine chain linked by Beta 1-4 glycosidic bonds with most acetyl groups removed from the number two positions to a 70–92% de-acetylation. Molecular weight determinations may be made by the method of Wu and Baugh (Journal of Chromatography 128, pages 87–99 (1976)). The degree of de-acetylation of the chitosan may be determined by the method of Hayes and Davies, Proceedings of The First International Conference on Chitin/Chitosan, 1978, pp. 193–199. Chitosan with defined physical and chemical properties may be prepared from any natural source of arthropod exoskeletans or fungal cell walls, by controlling the processes of de-acetylation and depolymerization.

The chitosan employed in this method may be purchased from Kypro, Inc., 208 Carlson Building, Bellevue, Wash. and identified as "CHITOSAN-High Viscosity". The chitosan employed in this method is a mixture of polymers with a molecular weight span from 10,000 through 2,055,000, and with individual molecules 78–92% de-acetylated. In those chitosans tested, the most abundant molecular species have a molecular weights of 1,487,000 to 1,682,000 and a number average of 129,000 to 322,000 with a dispersity of 5. The product is 78–92% de-acetylated with a mean of 85% deacetylation. Chitosan in solution, and solid chitosan as fibers, sheets or powders were used.

Although the chitosan employed in the various experiments set forth herein was purchased from Kypro, Inc., the term "chitosan" is used by several suppliers to denote a product derived by partially de-acetylating chitin. It is with the chitosan purchased from the various sources that the experiments herein began.

The methods of preparing the chitosan so it could be used in the various experiments are described in detail hereinafter with the preferred preparation methods and proportions being described. However, Table A set forth hereinbelow lists the characteristics (preferred and permissible) of the chitosan material of this invention.

Chitosans with various sources of origin, states of depolymerization and/or states of de-acetylation were dissolved at a concentration of 2 grams per liter, in distilled water containing the minimum quantity of acetic acid necessary to dissolve the solid material. The preferred hemostatic chitosan solution is prepared by dissolving 2 grams of chitosan in 998.5 milliliters of distilled water and 1.5 milliliters of glacial acetic acid. The mixture is stirred at room temperature for 2 to 3 hours to produce a clear chitosan solution in 0.026N acetic acid having a pH of 4.1±0.2 Preferably, the solution is stored at 4° C. Hemostatic chitosan fiber mats were prepared by placing an appropriate quantity of sterile solution in sterile siliconecoated tubes, crystallizing the solution at −60° C. and freeze drying. By varying the diameter of the tubes and placing them upright or on their sides in the freezer, the preparation of short dense plugs or long thin strips were obtained. Preferably, 2.5 milliliters of the chitosan solution was utilized to yield 5 milligram mats. Chitosan films were prepared by drying thin layers of solution on flat teflon plates without freezing. It has been found that flat fiber mats are easier to handle than films. Chitosan hemostatic powders were prepared by grinding the mats with sterile mortar and pestle. The chitosan hemostatic agent was incorporated into sheets of fabric and tubular grafts by soaking the same in the chitosan solution thereby yielding surface adhesion or by drying the chitosan fibers or amorphous chitosan into the interstices of the fabrics.

The chitosan hemostatic solution may be sterilized by filtration through 2-micron filters; however, the process is slow and the yield is low. Steam autoclaving of chitosan solutions produces a marked decrease in coagulum-forming effectiveness. Chitosan acetate and chitosan hydrochloride solutions and lyophilized solids (salts) are heat labile about 100° C., so chitosan hemostatic solutions, fibers, powders and films should be prepared from sterile chitosan rather than being sterilized after preparation. The best chitosan used in these experiments described herein was heat stable and was sterilized in a steam autoclave at 250° F. for fifteen minutes.

The inventors herein have discovered that chitosan from shrimp, two species of crab, and two unknown sources ("chitosan practical grade") formed a hemostatic coagulum when acid solutions of various concentrations were brought into contact with blood in test tubes or in skin incisions in dogs. Chitosan which was only 42% de-acetylated required up to 1.0N acid for solution (with some solid residue). Polyglucosamine (100% de-acetylated chitosan) formed a good coagulum; however, only small quantities were tested. Lower and medium viscosity chitosans were easily dissolved and quickly sterilized by membrane filters; however, stability of the coagulum was directly proportional to the molecular weight of the most prevalent polymer in the solution. The following experiments were conducted and the experiments support the theory that chitosan prevents fibroplasia and does promote tissue regeneration.

In the patents of Balassa Nos. (3,914,413; 3,911,116; and 3,903,268) rats were treated with chitin derivatives (not chitosan), given as solids into the wounds. Prudden's method of tissue tensile strength measurement was used. A balloon was introduced into the abdominal cavity of treated and untreated rats at intervals of five days, seven days and eleven days. The ballons were inflated until the wounds disrupted. The bursting pressure in millimeters of mercury was the index of tensile strength. The original work of Prudden and Balassa claimed increased tensile strength in cartilage treated rats (over controls) of 20 to 40% at five and seven days, but no difference at eleven days. In the Balassa patents, increases of 25% are claimed when chitin is used.

Experiment I

For our first experiment, fifty-four rats were paired by body weight. One rat's incision was sponged with our chitosan solution (200 mg/100 cc in 0.026N acetic acid) and the other with physiological saline. About one cubic centimeter of viscous chitiosan solution containing 2 milligrams of chitosan stuck to the sides of the abdominal wound. Although we planned nine pairs for each evaluation day, four animals died; leaving eight pairs for days 5 and 7, and including one "rematched" pair within 9 grams initial weight in the eight pairs for day 11.

The results of the chitosan hemostatic solution wound healing evaluation are depicted in FIG. 1. After five days, we found that six of the eight chitosan treated rats' wounds burst at lower intra-abdominal pressures than their paired control rats. The sum (6 minuses and 2 pluses) of pressure differences between chitosan and control rats was divided by eight to yield a mean bursting pressure decrease of minus 14.4 mm. Hg. This was divided by the mean control bursting pressure to yield an 11% decrease in the tensile strength of wounds in the chitosan treated rats. At 7 days, five of the eight chitosan treated rats' wounds burst at lower pressures than their paired controls. Computation yielded an insignificant 6.4% decrease in tensile strength. At 11 days, five of the chitosan treated rats' wounds burst at slightly higher pressures than the controls. Computation yielded an insignificant 2% decrease in tensile strength.

Experiment II

Our second experiment was an attempt to apply chitosan fiber mats to the standard Prudden abdominal wound. With teflon-coated tweezers, we were able to lay 4 milligrams of matted chitosan fibers along one edge of each standard abdominal wall incisions in female rats. Closing the wounds with suture resulted in an irregular application of the solid chitosan; however, some portion of each mat was directly between opposing wound edges. Control animals had nothing added to the wound edges. Evaluation at 5 days revealed that chitosan-treated wounds were grossly deficient in wound healing compared to the controls. In places where the mat had blocked the formation of a blood clot across the wound, wounds broke during insertion of the balloon. When the balloon could be inserted without disrupting the treated wound, the wounds broke irregularly (rather than burst) at much lower pressures than control rats' wounds.

The prior art teaches that N-acetylated partially depolymerized chitin materials facilitate early wound healing by increasing the tensile strength (resistance to disruption) in the early stages of wound healing (5, 7 and 11 days). We have found that chitosan hemostatic solution and chitosan hemostatic fiber mats interfere with early wound healing by decreasing the tensile strength in the earliest stage of wound healing (5 days); and that chitosan hemostatic solution has no significant effect on wound healing at later stages (7 and 11 days).

Experiment III

It is well known that porous synthetic vascular grafts, when placed in artery segments, heal by fibrosis. A layer of fibrous tissue and fibrin coat the inside of the structure with another fibrous coating on the outside.

The tissue is in effect an avascular scar surrounding a foreign body and as such it does not grow or replenish itself as living tissue would do. It is with this in mind that the experiment was conducted. Porous knitted Dacron Debakey grafts were placed in the infrarenal aorta of dogs. Controls were also placed without chitosan solution. The experimental grafts were simply soaked in chitosan hemostatic solution as previously described. After 1, 2, 3 and 4 months, both groups of grafts were examined grossly and by light and electron microscopy. The control grafts were encased in avascular fibrous tissue.

The chitosan treated grafts were encased in smooth muscle which penetrated the graft interstices. The graft was lined with living endothelial cells, numerous blood vessels (vasa vasovum) supplied this tissue and there was ingrowth of myelinated nerve fibers. In brief, it was found that diverse tissue elements of normal artery regenerated de novo. Thus, these experiments indicated that chitosan when applied to vascular grafts results in the inhibition of fibroplasia and promotes the regeneration of normal tissue elements.

Dogs that were completely anticoagulated (blood clotting times greater than one hour) by sodium heparin injection prior to the operation showed no leakage of blood through the porous graft. Regeneration of a smooth muscle wall around the graft was observed at 1, 2, 3 and 4 months.

Experiment IV

Skin wounds 2 cm. long were made in the abdominal skin penetrating through the subcutaneous tissue in five healthy mongrel dogs. Each dog received four wounds. One wound was treated only with a saline compress, one with a standard hemostatic agent (gelatin foam), one with the described chitosan solution and one with chitosan solution fiber mats. The wounds were examined immediately and at intervals of 24 hours, 72 hours, seven days and at one month. Gross examination and light microscopy were done. The saline control wound resulted in the usual broad scar. The wound with the hemostatic agent revealed that the gelatin foam remained in the wound with severe tissue reaction. Solid chitosan revealed a scar similar to that of gelatin foam. The wounds treated with chitosan solution healed with thin scars.

Experiment V

Incised wounds 2 cm. long and 1 cm. deep were made in the left rectus abdominus muscle of five healthy mongrel dogs. As in Example IV, the wounds were treated with saline compress, hemostatic agent, chitosan solution, and chitosan fiber mats. The examination intervals were immediate, 24 hours, 72 hours, seven days and 30 days. Gross examination and light microscopy were utilized to determine the amount of scar tissue present. Since muscle retracts when cut, the tissue defect was quite wide. The saline treated muscle wound resulted in a wide scar. The wound treated with the standard hemostatic agent revealed severe tissue reaction with remnants of the gelatin foam still present at one month. The wounds treated with chitosan solution and lyophylized chitosan revealed less scar tissue and muscle proliferation.

Experiment VI

Incised wounds 2 cm. long and 1 cm. deep were made in the liver of five healthy mongrel dogs. The wounds were treated with a standard hemostatic agent, chitosan solution, and lyophylized chitosan. The wounds were examined at intervals grossly and with light microscopy. The wound treated with the hemostatic agent revealed severe scarring and the hemostatic material was still in the wound at one month. The wounds treated with chitosan solution and lyophylized chitosan revealed smaller scars and some regeneration of hepatic tissue.

Experiment VII

Incised wounds 2 cm. long and 1 cm. deep were made in the spleen of five healthy mongrel dogs. These wounds were treated with the standard hemostatic agent, the described chitosan solution and the lyophylized chitosan. Examination of the wounds at intervals grossly and by light microscopy revealed that the wound treated with the standard hemostatic agent contained severe tissue reaction with scarring and retained hemostatic agent. The wounds treated with chitosan solution and lyophylized chitosan revealed practically no tissue reaction and small scars.

Experiment VIII

Identical avulsions (scoop wounds) were made in the right and left parietal lobes of the brains of mongrel cats. The chitosan hemostatic of this invention was as effective in achieving hemostasis as other liquid (thrombin solution) and solid hemostatic agents. At the end of one month, the chitosan wounds in which hemostasis was best showed less fibrous scar, fewer pigment-laden macrophages, and a greater number of glial elements.

Experiment IX

The chitosan hemostatic solution of this invention was applied to exposed bone marrow surfaces in the hips of dogs and the solution stopped the blood from oozing over the surface. At one week, the control sites were covered by an organized thick blood clot containing many macrophages and fibroblasts. The chitosan treated surfaces were coated by a thin coagulum containing fewer macrophages and fibroblasts. The chitosan solution was also injected into the traumatized hip joint of a mongrel dog. At one week, there were fewer blood and inflammatory cells in the joint fluid than in the 0.026N acetic acid control joint.

The foregoing experiments reveal that chitosan whether in solution in pH 4 acetic acid, fiber mats, or powders, inhibits fibroplasia, and promotes tissue regeneration while achieving hemostasis.

Table A hereinbelow lists the various characteristics of the chitosan solution to enable the desired hemostasis, inhibition of fibroplasia and promotion of tissue regeneration to be achieved.

TABLE A

| Characteristic | Preferred | Permissible |
|---|---|---|
| Source | Dungness crabs | Arthropods or Fungi |
| Deacetylation | 85% | 42 to 100% |
| Molecular Weight Range | 10,000 to 2,055,000 | 10,000 to 2,055,000 |
| Molecular Weight of Most Abundant Species | 1,600,000 | 900,000 to 1,800,000 |
| Concentration | 2 grams per liter | 0.5 to 8 grams per liter |
| pH | 4 | 1 to 8 |
| Solute Concentration | Hypotonic | Hypotonic to Hypertonic* |

TABLE A-continued

| Characteristic | Preferred | Permissible |
|---|---|---|
| Acid | Acetic | Hydrochloric, sulphuric, phosphoric, organic |
| Acid Concentration | 0.026 N | 0.02 to 1.0 N |

Permissible ranges are not independently variable. Chitosans of high molecular weight and lower deacetylation will require higher acid concentrations just to put the material into solution.
*compared to normal blood solute concentration.

The conclusions to be reached by studying Experiments I–IX hereinabove are that the chitosan of this invention does achieve hemostasis, does inhibit fibroplasia and does promote tissue regeneration.

We claim:

1. The method of inhibiting fibroplasia and promoting tissue regeneration in vascular grafts which comprises placing, an effective amount of chitosan in contact with the graft, said chitosan being between 42 to 100 percent deacetylated; said chitosan having a molecular weight range of 10,000 to 2,055,00; said chitosan being soluble in distilled water and an acid selected from the group of hydrochloric, sulphuric, phosphoric and organic acid having an acid concentration of 0.02 to 1.0N; said chitosan solution having a pH of 1 to 8.

2. The method of claim 1 wherein the chitosan is incorporated in the graft material.

3. The method of inhibiting fibroplasia and promoting tissue regeneration in a wound which comprises placing in contact with said wound an effective amount of chitosan, said chitosan being between 42 to 100 percent deacetylated; said chitosan having a molecular weight range of 10,000 to 2,055,00; said chitosan being soluble in distilled water and an acid selected from the group of hydrochloric, sulphuric, phosphoric and organic acid having an acid concentration of 0.02 to 1.0N; said chitosan solution having a pH of 1 to 8.

4. The method of claim 3 wherein said chitosan is 78 to 92% deacetylated.

5. The method of claim 3 wherein the chitosan is in solution with distilled water and acetic acid and has a pH of approximately 4.

6. The method of claim 3 wherein said chitosan is in solid form.

7. The method of claim 6 wherein said chitosan is a salt prepared by dehydrating an acid solution of chitosan.

8. The method of claim 7 wherein said chitosan comprises a powder.

9. The method of claim 7 wherein said chitosan is a film.

10. The method of claim 7 wherein said chitosan is a sheet.

11. The method of claim 7 wherein said chitosan is in fiber form.

12. The method of claim 11 wherein said chitosan fibers are formed into mats.

13. The method of claim 11 wherein said chitosan fibers are formed into plugs.

14. The method of claim 3 wherein the blood of the wounded subject is anticoagulated.

15. The method of claim 3 wherein the wound is locally anticoagulated.

16. The method of achieving hemostasis, inhibiting fibroplasia and for promoting tissue regeneration in a wound which comprises placing an effective amount of polyglucosamine in contact with the wound.

* * * * *

UNITED STATES PATENT AND TRADEMARK OFFICE
CERTIFICATE OF CORRECTION

PATENT NO. : 4,532,134
DATED : July 30, 1985
INVENTOR(S) : Malette, et al.

It is certified that error appears in the above-identified patent and that said Letters Patent is hereby corrected as shown below:

In the <u>cover page</u>, <u>1st column</u>, under the section entitled Notice, change the sentence "The portion of the term of this patent subsequent to July 19, 2000 has been disclaimed." to read as - - The portion of the term of this patent subsequent to the termination date of U.S. Patent No. 4,394,373, April 6, 2001, has been disclaimed. - - .

Signed and Sealed this

Eighth Day of May, 2001

*Attest:*

NICHOLAS P. GODICI

*Attesting Officer*   Acting Director of the United States Patent and Trademark Office